(12) United States Patent
Mault et al.

(10) Patent No.: US 6,513,532 B2
(45) Date of Patent: Feb. 4, 2003

(54) DIET AND ACTIVITY-MONITORING DEVICE

(75) Inventors: James R. Mault, Evergreen, CO (US); Edwin Pearce, San Francisco, CA (US); David Gilmore, San Francisco, CA (US); Roshi Givechi, San Francisco, CA (US); Jeanne Ragan, Plymouth, MI (US); Andrzej Skoskiewicz, Menlo Park; Neil Grimmer, San Francisco, both of CA (US)

(73) Assignee: Healthetech, Inc., Golden, CO (US)

( * ) Notice: Subject to any disclaimer, the term of this patent is extended or adjusted under 35 U.S.C. 154(b) by 0 days.

(21) Appl. No.: 09/745,373

(22) Filed: Dec. 23, 2000

(65) Prior Publication Data

US 2001/0049470 A1 Dec. 6, 2001

Related U.S. Application Data

(60) Provisional application No. 60/251,179, filed on Dec. 5, 2000, provisional application No. 60/243,621, filed on Oct. 26, 2000, provisional application No. 60/240,185, filed on Oct. 13, 2000, provisional application No. 60/230,860, filed on Oct. 7, 2000, provisional application No. 60/234,866, filed on Sep. 22, 2000, provisional application No. 60/212,319, filed on Jun. 16, 2000, provisional application No. 60/209,921, filed on Jun. 7, 2000, provisional application No. 60/207,051, filed on May 25, 2000, provisional application No. 60/207,089, filed on May 25, 2000, provisional application No. 60/201,902, filed on May 4, 2000, provisional application No. 60/200,428, filed on Apr. 28, 2000, provisional application No. 60/195,779, filed on Apr. 10, 2000, provisional application No. 60/194,126, filed on Apr. 3, 2000, provisional application No. 60/179,882, filed on Feb. 2, 2000, provisional application No. 60/178,979, filed on Jan. 28, 2000, and provisional application No. 60/177,016, filed on Jan. 19, 2000.

(51) Int. Cl.⁷ .......................... G06F 17/00; A61B 5/103; A61B 5/112

(52) U.S. Cl. ........................................ 128/921; 600/595
(58) Field of Search ............................... 600/595, 587, 600/300, 301; 128/920–921

(56) References Cited

U.S. PATENT DOCUMENTS

| | | | |
|---|---|---|---|
| 3,972,038 A | 7/1976 | Fletcher et al. | 340/189 M |
| 4,100,401 A | 7/1978 | Tutt et al. | 235/92 T |
| 4,101,071 A | 7/1978 | Brejnik et al. | 235/92 MT |
| 4,117,834 A | 10/1978 | McPartland et al. | 128/2 S |
| 4,159,416 A | 6/1979 | Brejnik et al. | 235/92 MT |
| 4,192,000 A | 3/1980 | Lipsey | 364/415 |
| 4,212,079 A | 7/1980 | Segar et al. | 364/900 |
| 4,221,959 A | 9/1980 | Sessier | |
| 4,224,952 A | 9/1980 | Sidorenko et al. | 128/782 |
| 4,244,020 A | 1/1981 | Ratcliff | 364/413 |
| 4,321,674 A | 3/1982 | Krames et al. | 364/413 |
| 4,353,375 A | 10/1982 | Colburn et al. | 128/782 |
| 4,380,802 A | 4/1983 | Segar et al. | 364/900 |
| 4,387,777 A | 6/1983 | Ash | 177/43 |

(List continued on next page.)

Primary Examiner—Kevin Shaver
Assistant Examiner—Navin Natnithithadha
(74) Attorney, Agent, or Firm—Gifford, Krass, Groh, Sprinkle, Anderson & Citkowski, P.C.

(57) ABSTRACT

A diet and activity-monitoring device includes a timer which outputs a time-indicative signal. A body activity monitor monitors the body activity of a subject and outputs a signal indicative of the body activity. A consumption notation control is provided which the subject may operate to indicate when they consume food. An activity calculator receives the body activity signal and determines a body activity level for the subject. A consumption calculator communicates with the consumption notation control and receives the time-indicative signal. The consumption calculator determines and stores the times when the consumption location control is operated.

39 Claims, 8 Drawing Sheets

U.S. PATENT DOCUMENTS

| | | | |
|---|---|---|---|
| 4,566,461 A | 1/1986 | Lubell et al. | 128/668 |
| 4,571,682 A | 2/1986 | Silverman et al. | 364/413 |
| 4,575,804 A | 3/1986 | Ratcliff | 364/715 |
| 4,629,015 A | 12/1986 | Fried et al. | 177/25 |
| 4,650,218 A | 3/1987 | Hawke | 283/67 |
| 4,686,624 A | 8/1987 | Blum et al. | 364/415 |
| 4,796,182 A | 1/1989 | Duboff | 364/413.29 |
| 4,803,625 A | 2/1989 | Fu et al. | 364/413.03 |
| 4,807,169 A | 2/1989 | Overbeck | 364/715.01 |
| 4,823,808 A | 4/1989 | Clegg et al. | 128/773 |
| 4,853,854 A | 8/1989 | Behar et al. | 364/413.01 |
| 4,855,942 A | 8/1989 | Bianco | 364/561 |
| 4,855,945 A | 8/1989 | Sakai | 364/709.02 |
| 4,891,756 A | 1/1990 | Williams, III | 364/413.29 |
| 4,894,793 A | 1/1990 | Ikemoto et al. | 364/709.03 |
| 4,911,256 A | 3/1990 | Attikiouzel | 177/25.16 |
| 4,924,389 A | 5/1990 | Gerbaulet et al. | 364/413.29 |
| 4,951,197 A | 8/1990 | Mellinger | 364/413.2 |
| 4,954,954 A | 9/1990 | Madsen et al. | 364/413.29 |
| 4,966,155 A | 10/1990 | Jackson | 128/671 |
| 5,012,411 A | 4/1991 | Policastro et al. | 364/413.04 |
| 5,033,561 A | 7/1991 | Hettinger | 177/25.16 |
| 5,173,588 A | 12/1992 | Harrah | 235/114 |
| 5,233,520 A | 8/1993 | Kretsch et al. | 364/413.29 |
| 5,263,491 A | 11/1993 | Thornton | 128/774 |
| 5,307,263 A | 4/1994 | Brown | 364/413.09 |
| 5,387,164 A | 2/1995 | Brown, Jr. | 482/9 |
| 5,388,043 A | 2/1995 | Hettinger | 364/413.29 |
| 5,398,688 A | 3/1995 | Laniado | 128/660.02 |
| 5,412,560 A | 5/1995 | Dennison | 364/413.01 |
| 5,412,564 A | 5/1995 | Ecer | 364/413 |
| 5,454,721 A | 10/1995 | Kuch | 434/127 |
| 5,478,989 A | 12/1995 | Shepley | 235/375 |
| 5,485,402 A | 1/1996 | Smith et al. | 364/566 |
| 5,542,420 A | 8/1996 | Goldman et al. | 128/630 |
| 5,640,774 A | 6/1997 | Goldman | 33/15 D |
| 5,673,691 A | 10/1997 | Abrams et al. | 128/630 |
| 5,678,562 A | 10/1997 | Sellers | 128/710 |
| 5,691,927 A | 11/1997 | Gump | 364/709.01 |
| 5,704,350 A | 1/1998 | Williams, III | 128/630 |
| 5,722,418 A | 3/1998 | Bro | 128/732 |
| 5,729,479 A | 3/1998 | Golan | 364/709.02 |
| 5,788,655 A * | 8/1998 | Yoshimura et al. | 600/587 |
| 5,819,735 A | 10/1998 | Mansfield et al. | 128/630 |
| 5,827,179 A | 10/1998 | Lichter et al. | 600/300 |
| 5,828,943 A | 10/1998 | Brown | 434/258 |
| 5,832,448 A | 11/1998 | Brown | 705/2 |
| 5,836,312 A | 11/1998 | Moore | 128/897 |
| 5,841,115 A | 11/1998 | Shepley | 235/375 |
| 5,845,263 A | 12/1998 | Camaisa et al. | 705/27 |
| 5,876,351 A | 3/1999 | Rohde | 600/523 |
| 5,890,128 A | 3/1999 | Diaz et al. | 705/2 |
| 5,899,855 A | 5/1999 | Brown | 600/301 |
| 5,908,301 A | 6/1999 | Lutz | 434/236 |
| 5,913,310 A | 6/1999 | Brown | 128/897 |
| 5,918,603 A | 7/1999 | Brown | 128/897 |
| 5,951,300 A | 9/1999 | Brown | 434/236 |
| 5,954,510 A | 9/1999 | Merrill et al. | 434/236 |
| 5,987,493 A | 11/1999 | Rangan et al. | 709/105 |
| 5,989,188 A | 11/1999 | Birkhoelzer et al. | 600/300 |
| 5,989,200 A * | 11/1999 | Yoshimura et al. | 600/587 |
| 5,997,476 A | 12/1999 | Brown | 600/300 |
| 6,013,007 A | 1/2000 | Root et al. | 428/8 |
| 6,014,578 A | 1/2000 | Minoz | 600/350 |
| 6,024,281 A | 2/2000 | Shepley | 235/375 |
| 6,024,699 A | 2/2000 | Surwit et al. | 600/300 |
| 6,030,342 A | 2/2000 | Amano et al. | 600/301 |
| 6,032,119 A | 2/2000 | Brown et al. | 705/2 |
| 6,032,676 A | 3/2000 | Moore | 128/898 |
| 6,039,688 A | 3/2000 | Douglas et al. | 600/300 |
| 6,040,531 A | 3/2000 | Miller-Kovach et al. | 177/25.16 |
| 6,042,383 A | 3/2000 | Herron | 434/238 |
| 6,045,513 A | 4/2000 | Stone et al. | 600/508 |
| 6,077,193 A | 6/2000 | Buhler et al. | 482/8 |
| 6,083,006 A | 7/2000 | Coffman | 434/127 |
| 6,095,949 A | 8/2000 | Arai | 482/4 |
| 6,095,985 A | 8/2000 | Raymond et al. | 600/513 |
| 6,101,478 A | 8/2000 | Brown | 705/2 |
| 6,135,950 A | 10/2000 | Adams | 600/300 |
| 6,135,951 A | 10/2000 | Richardson et al. | 600/300 |
| 6,139,494 A | 10/2000 | Cairnes | 600/300 |

\* cited by examiner

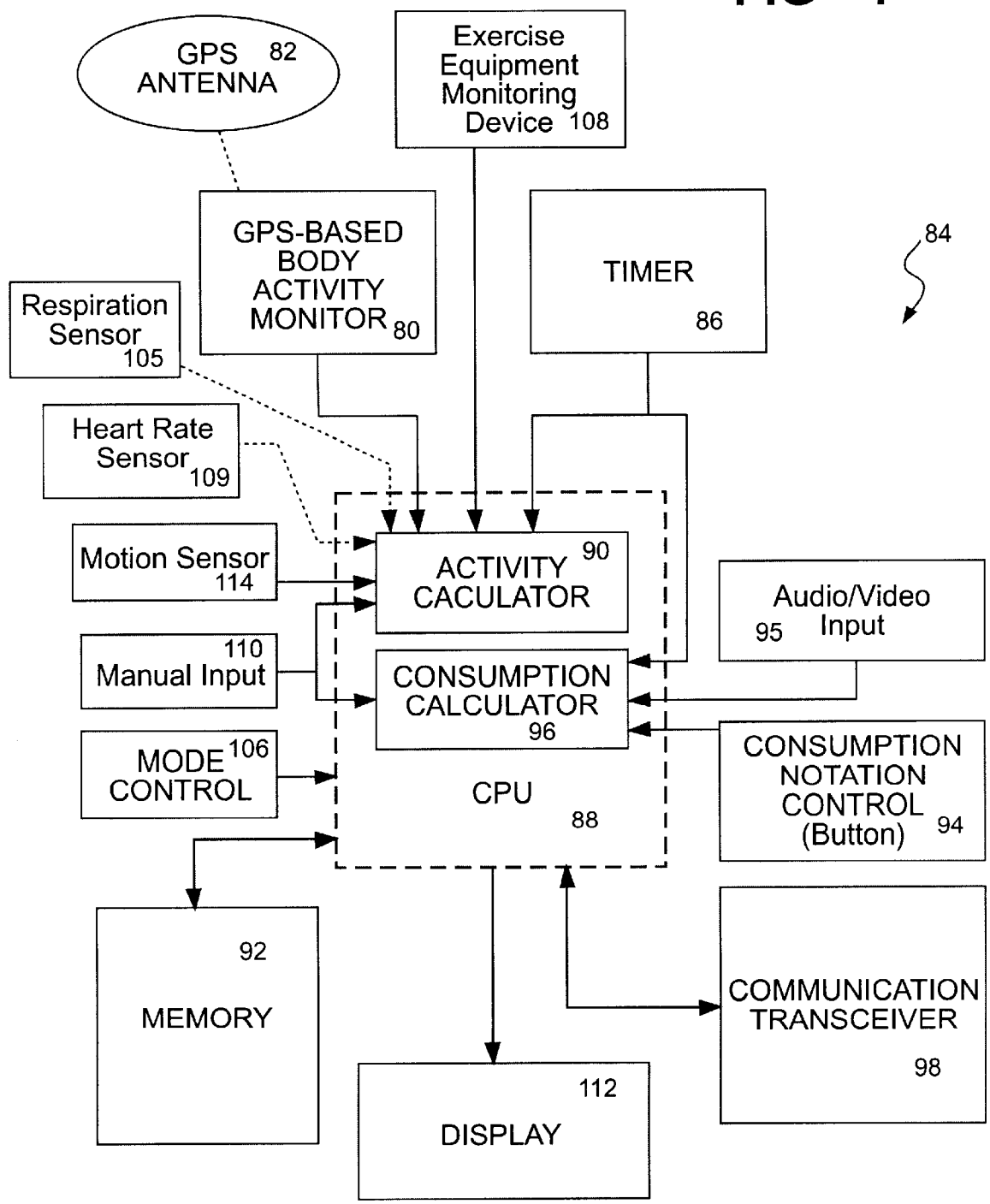

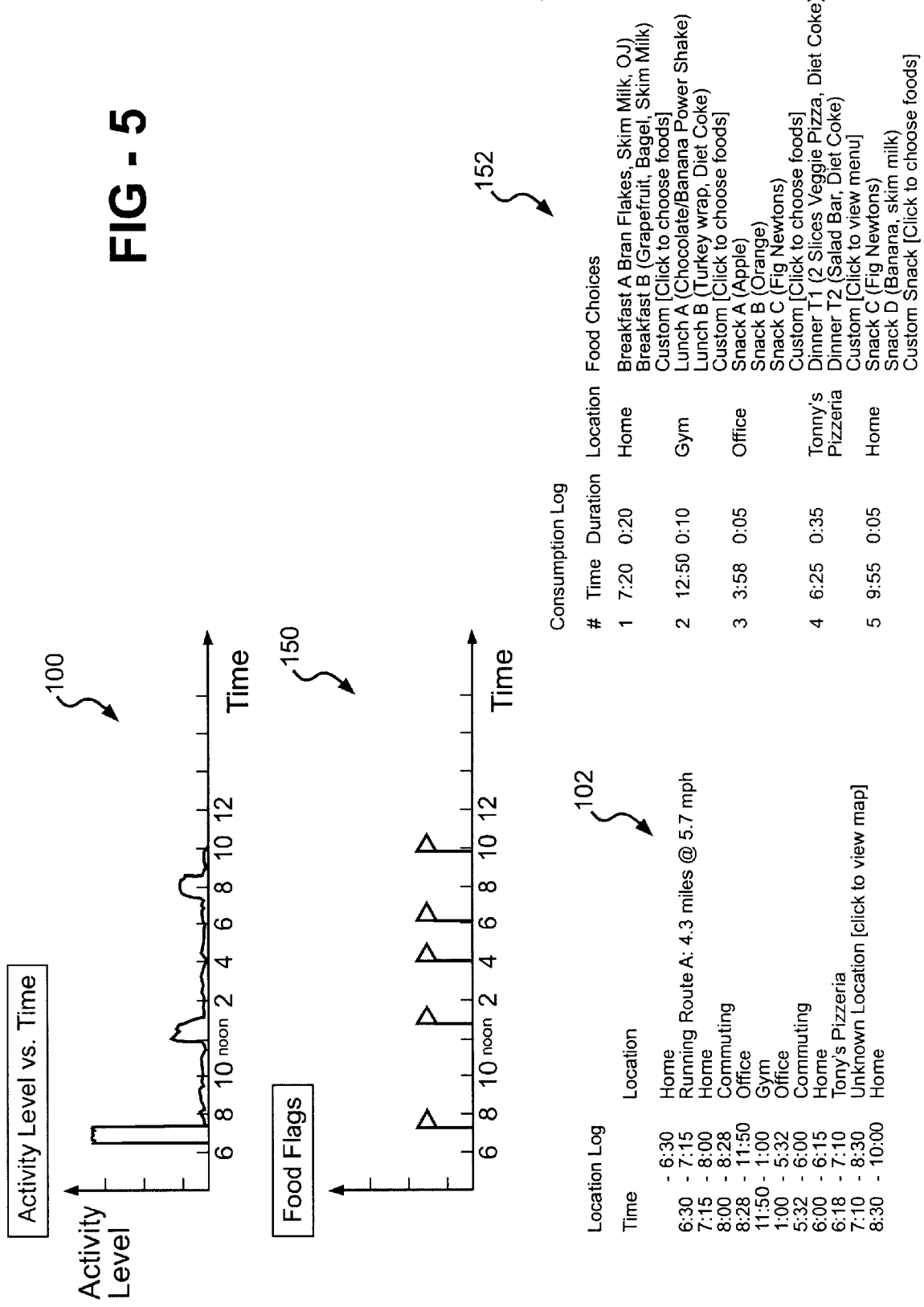

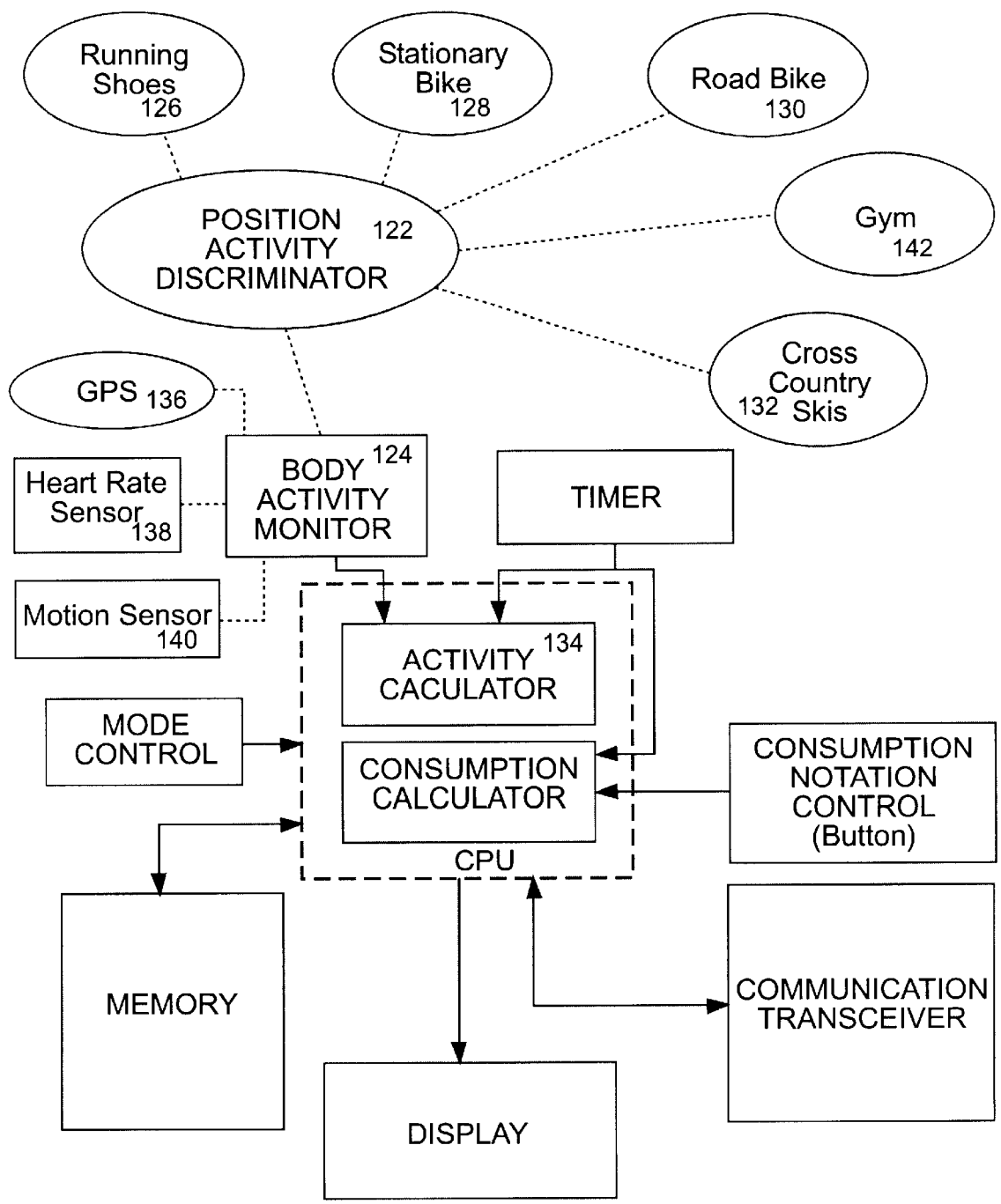

US 6,513,532 B2

DIET AND ACTIVITY-MONITORING DEVICE

This application claims priority from U.S. provisional patent applications Ser. Nos. 60/177,016, filed Jan. 19, 2000; 60/178,979, filed Jan. 28, 2000; 60/179,882, filed Feb. 2, 2000, 60/195,779, filed Apr. 10, 2000; 60/194,126, filed Apr. 3, 2000; 60/209,921, filed Jun. 7, 2000; 60/200,428, filed Apr. 28, 2000; 60/201,902, filed May 4, 2000; 60/207,089, filed May 25, 2000; 60/207,051, filed May 25, 2000; 60/212,319, filed Jun. 16, 2000; 60/234,866, filed Sep. 22,2000; 60/230,860, filed Sep. 7, 2000; 60/240,185, filed Oct. 13, 2000; 60/243,621, filed Oct. 26, 2000 and 60/251,179, filed Dec. 5, 2000, all of which are incorporated herein in their entirety by reference. This application also claims priority from U.S. patent application Ser. Nos. 09/685,625, filed Oct. 10, 2000; 09/630,398, filed Aug. 2, 2000; 09/669,125 filed Sep. 25, 2000; 09/684,440 filed Oct. 10, 2000; and 09/721,382 filed Nov. 22, 2000, are also incorporated herein in their entirety by reference.

FIELD OF THE INVENTION

The present invention relates generally to activity monitors and diet monitors and, more specifically, to a device that combines both diet and activity monitoring.

BACKGROUND OF THE INVENTION

Management of diet, health, and fitness has drawn increasing amounts of attention as their importance has been recognized, and as consumers around the world have struggled to balance busy lives with fitness and proper diet. Despite the recognized importance of good health, consumers, on average, are becoming increasingly obese. This has resulted in a strong demand for devices and methods that assist individuals in setting and reaching dietary and fitness goals. Currently available devices and methods fail to meet the needs of average consumers.

There are serious problems with conventional weight loss programs. Weight change is related to the user's net caloric balance, the difference between caloric intake and caloric expenditure. However, determination of caloric intake and caloric expenditure are both problematic.

There are numerous difficulties in accurately determining caloric intake. In some diet programs printed or electronic lists are used that provide the nutrition content of a wide variety of food. The consumer keeps a diet log of all foods consumed each day in order to determine their total nutritional intake. These systems typically are laborious to use and only the most dedicated consumer will accurately use these approaches. For example, a consumer must take the time to accurately record the foods consumed each day. Obviously, recognition of foods consumed is most accurate if done at the time the foods are consumed. However, many individuals feel too rushed to record the foods consumed at the time and postpone recording for later in the day or week. Also, some consumers are embarrassed to be observed recording food intake during or following a meal. This also motivates the user to wait to record their consumption until later. Obviously, accuracy suffers the more time passes between consumption and recordation. An individual may entirely forget that they had a snack or two earlier in the day or week, leading to undercounting of consumption.

Determining total energy expenditure is also difficult. The total energy expenditure of a person comprises a resting metabolic component and a physical activity component. Total energy expenditure (TEE) is the sum of resting energy expenditure (REE) and activity energy expenditure (AEE), i.e. TEE=AEE+REE. Weight loss occurs if total energy expenditure (TEE) exceeds total caloric intake over a given time period. As discussed by Remmereit in U.S. Pat. No. 6,034,132, 70 percent of total energy expenditure for a typical person is due to their resting metabolic rate (RMR). In a conventional diet program, RMR is estimated from the height, weight, age, and gender of the person, for example using the Harris-Benedict equation. This equation, well known to those skilled in the nutritional arts, is given in U.S. Pat. No. 5,839,901 to Karkanen, and in U.S. Pat. No. 5,639,471 to Chait et al. There are serious inadequacies in using the Harris-Benedict equation (or any similar equation) in a weight loss program. The Harris-Benedict equation provides only an estimated RMR, which is an average value for people of similar height, weight, age, and gender. However, due to natural variations in physiology, the equation may not be accurate for a specific individual.

Conventional weight loss programs use an estimated total energy expenditure (TEE) based on estimates of activity levels, and estimates of resting energy expenditure (REE) from the Harris-Benedict equation. However, unless the resting energy expenditure (REE) and the activity energy expenditure (AEE) are estimated accurately, the person's caloric balance cannot be known accurately, and the outcome of a weight loss program is likely to be unsatisfactory.

Some users attempt to track their activity energy expenditure (AEE), either for weight loss or general fitness purposes. In the simplest approach the individual maintains an exercise log of activities conducted, such as distances walked or jogged. Various graphs and tables can then provide an estimate of the calories burned during these activities. As with recording consumption, an individual may fail to accurately record the type and duration of activity undertaken leading to inaccurate recordation. Also, an individual may not know how far or fast they ran or walked. A variety of pedometers are available to assist with this task. Pedometers include some type of stride counter in order to count the number of strides or paces taken by the individual. The devices may be calibrated to allow them to determine the distance traveled with reasonable accuracy. Through the use of timers, they may also be able to determine the speed and duration of activity. Pedometers typically fail to take into consideration changes of elevation, changes in length of stride and changes in intensity. For example, a runner may combine slow walking with brisk running during an exercise session. By combining total number of strides and duration of activity, the pedometer may only determine average speed, not instantaneous speed.

U.S. Pat. Nos. 6,002,982 and 6,148,262 to Fry; U.S. Pat. No. 6,013,007 to Root et al; U.S. Pat. Nos. 6,009,138 to Slusky; and U.S. Pat. Nos. 6,032,108 to Seiple et al each disclose improved activity monitors utilizing a global positioning system (GPS). The devices track an individual's position over time, using the GPS network. By periodically or instantaneously comparing position and time, such a device is capable of determining a performance profile with better accuracy than a typical pedometer.

Devices are also available for monitoring and tracking heart rate. The most popular of these devices are sold by Polar Electro Oy of Finland. These heart rate monitors includes a wristwatch-style display unit and a chest strap with a heart rate sensor. The chest strap and display unit communicate wirelessly. The devices are capable of accurately monitoring heart rate, which correlates reasonably well with exercise intensity. Advanced devices include the ability to track heart rate over time so that a heart rate profile may be produced.

Each of the above-discussed activity monitors fails to consider the dietary intake portion of total health management. Instead, they are directed merely to activity monitoring. In light of this, there remains a need for a device that combines activity monitoring and diet monitoring, that is easy to use and provides accurate results.

SUMMARY OF THE INVENTION

The present invention improves on the prior art by providing a combination diet and activity monitoring device for monitoring both the consumption and activity of the subject. The effectiveness of weight management programs may be improved through a more accurate determination of caloric balance. Improved determination of caloric balance may be obtained by more accurate determinations of total energy expenditure, (the sum of resting energy expenditure and activity energy expenditure) and caloric intake. The present invention focuses on improving the determination of activity energy expenditure and caloric intake. Resting energy expenditure, the energy expended by an individual at rest, may be accurately determined using an indirect calorimeter, such as described in co-pending patent application Ser. No. 09/630,398, incorporated herein by reference. As discussed in this application, resting energy expenditure is based on resting metabolic rate. Resting metabolic rate changes over time, especially when the subject changes their diet or exercise patterns. Therefore, it is preferable to periodically measure resting metabolic rate so that accurate determinations of resting energy expenditure are available during a weight management program.

Determination of activity energy expenditure, which combined with resting energy expenditure provides total energy expenditure, may be obtained by monitoring a subject's activity on a regular basis. The monitoring device according to the present invention includes a body activity monitor for monitoring the body activity of the subject. The body activity monitor is operable to output a signal indicative of the subject's body activity. An activity calculator may also be provided, which receives the activity; indicative signal and determines a body activity level and/or energy expenditure for the subject. The body activity monitor may be integral with the monitoring device, or may be part of an auxiliary device. For example, the monitoring device according to the present invention may take the form factor of a wristwatch-style device or a belt or clothing-mounted monitor. In a wristwatch-style device, the body activity monitor may comprise a heart rate monitor, monitoring the heart rate of the subject. The heart rate of the subject increases with activity and decreases when the subject is resting. By calibrating the activity monitor, the subject's activity level and activity related energy expenditure may be determined. The activity monitor may be calibrated using an indirect calorimeter, as described in co-pending patent application Ser. No. 09/684,440, incorporated herein by reference. The heart rate monitor may form part of the wristwatch-style monitoring device and sense heart rate in the subject's wrist or other appendage. Alternatively, a separate heart rate sensor may be provided such as a chest strap, that communicates with the monitoring device, preferably using a wireless link. A belt or clothing mounted monitoring device may also include a heart rate monitor as the body activity monitoring portion.

The body activity monitor which forms part of the monitoring device according to the present invention may alternatively comprise a motion sensor such as a mechanical pendulum or a single or multi axis accelerometer. An accelerometer is preferred as it may provide information on body movement as well as the direction and intensity of the movement. The motion sensor may form part of the wristwatch or belt or clothing mounted monitoring device or may be part of a separate accessory that communicates with the monitoring device. For example, if the monitoring device according to the present invention takes the form of a belt or clothing mounted housing, the accelerometer may be disposed in the housing and sense motion of the housing. Because the housing is attached to the subject's belt or clothing, motion of the housing correlates with movement of the subject. Once again, the body activity monitor may be calibrated to determine activity related energy expenditure using an indirect calorimeter.

As another alternative, the body activity monitor may include multiple modes for recording of variety of activities, such as swimming, biking, and use of stationary exercise equipment. The body activity monitor may then be placed in the mode corresponding to an activity that the subject undertakes. The subject presses a start button and the body activity monitor will record the duration of the activity. The monitoring device may then determine an activity level based on the duration of the activity and the estimated intensity. The activity level may be adjusted by the user to increase the accuracy of the estimate. Alternatively, the body activity monitor portion of the monitoring device may communicate with the exercise equipment or system of equipment being used by the subject to allow transfer of accurate data related to exercise. As one simple alternative, the body activity monitor may allow the subject to create time-stamped exercise flags, corresponding to when exercise is undertaken. To create an exercise flag, the subject manipulates a control on the monitoring device at the time of the activity. Later, the time or the duration of the activity may be recalled and an actual activity level be entered for tracking purposes.

It is preferred that the monitoring device according to the present invention forms part of the system including a local remote computing device to which data from the monitoring device may be downloaded for further manipulation. For example, at the end of the day, the subject may download data from the monitoring device to a home PC. The subject may then view the activity and consumption data and have it during the day. The subject may then be prompted to provide additional information about events such as exercise and food flags. This data may be used as part of a determination of total caloric balance and as part of a weight loss program.

The monitoring device according to the present invention also preferably includes a consumption notation control for use by the subject to indicate when the subject consumes food. This consumption notation control preferably provides a very simple means for the subject to note when consumption occurs and avoids the embarrassment and difficulty of recording the actual foods consumed during or immediately following consumption of the foods. In one embodiment of the present invention, the subject manipulate a control on the monitoring device each time they consume food, whether the food is a snack or a meal. The monitoring device records the time the control was manipulated and creates a "food flag". Later, the subject may use the food flags to help them recall what they ate. Software on the local or remote computing device may assist in theses determinations by presenting options on what was consumed based on past behavior and software settings. Alternatively, food flags may also have a duration component. For example, a subject may manipulate the consumption notation control once at the beginning of the consumption event and again at the end of the consumption event. The duration of the event provides additional data for use in determining what foods were consumed. As another alternative, the consumption notation control may include and audio and/or video recording device, allowing the subject to make audio and/or video notations as to what was consumed. For example, the monitoring device may include a recording mechanism such as a digital recording means. In addition to or alternatively to the food flags, the subject may make a brief audio recording as to what was consumed. Alternatively, or additionally the monitoring device may include a video recording system such as a miniaturized camera. The subject may then photograph what was consumed to allow an accurate determination of consumption at a later time. The use of audio or video recording allows additional functionality. For example, the local or remote computing device may be operable to provide voice recognition on downloaded audio files from the monitoring device. Then, the subject's auditory notes may be transcribed into written text for later reference by the user. Alternatively, the software may determine what foods were consumed based on the auditory notation. Similar functionality may be provided with video recordings such as digital pictures. The digital pictures may be transmitted to a remote site where an administrative person reviews the picture and records what was consumed and transmits this recording back to the subject. This may be provided on a subscription basis. Alternatively, software could be provided which performs an image analysis on the digital picture to assist in determining the foods consumed. As another alternative, the monitoring device according to the present invention may include a scanning device to allow it to scan and record bar codes and similar coded markings. This functionality may be incorporated into the digital camera or may be separate. Also, the scanner may form a separate unit from the remainder of the monitoring device and communicate with the monitoring device through a wire or wireless connection. The bar code scanning may be used to scan foods to be consumed as well as other information such as data concerning exercise.

The monitoring device according to the present invention preferably also includes a timer that outputs a time indicative signal for use in time stamping food flags and exercise flags and for use in tracking activity during the day.

The diet and activity monitoring device may communicate with local and remote computers using a wired or wireless connection, as well as through transfer of memory modules. The local or remote computers may allow additional or easier access to advance functions, such as diet and activity tracking over longer periods of time.

BRIEF DESCRIPTION OF THE DRAWINGS

FIG. 4 is a schematic of another embodiment of a monitoring device according to the present invention;

FIG. 5 is a sample screen view of a local or remote computing device showing one version of a display of diet- and activity-related data;

FIG. 6 is a schematic of yet another embodiment of a monitoring device according to the present invention;

DETAILED DESCRIPTION OF THE PREFERRED EMBODIMENTS

Figure 1:
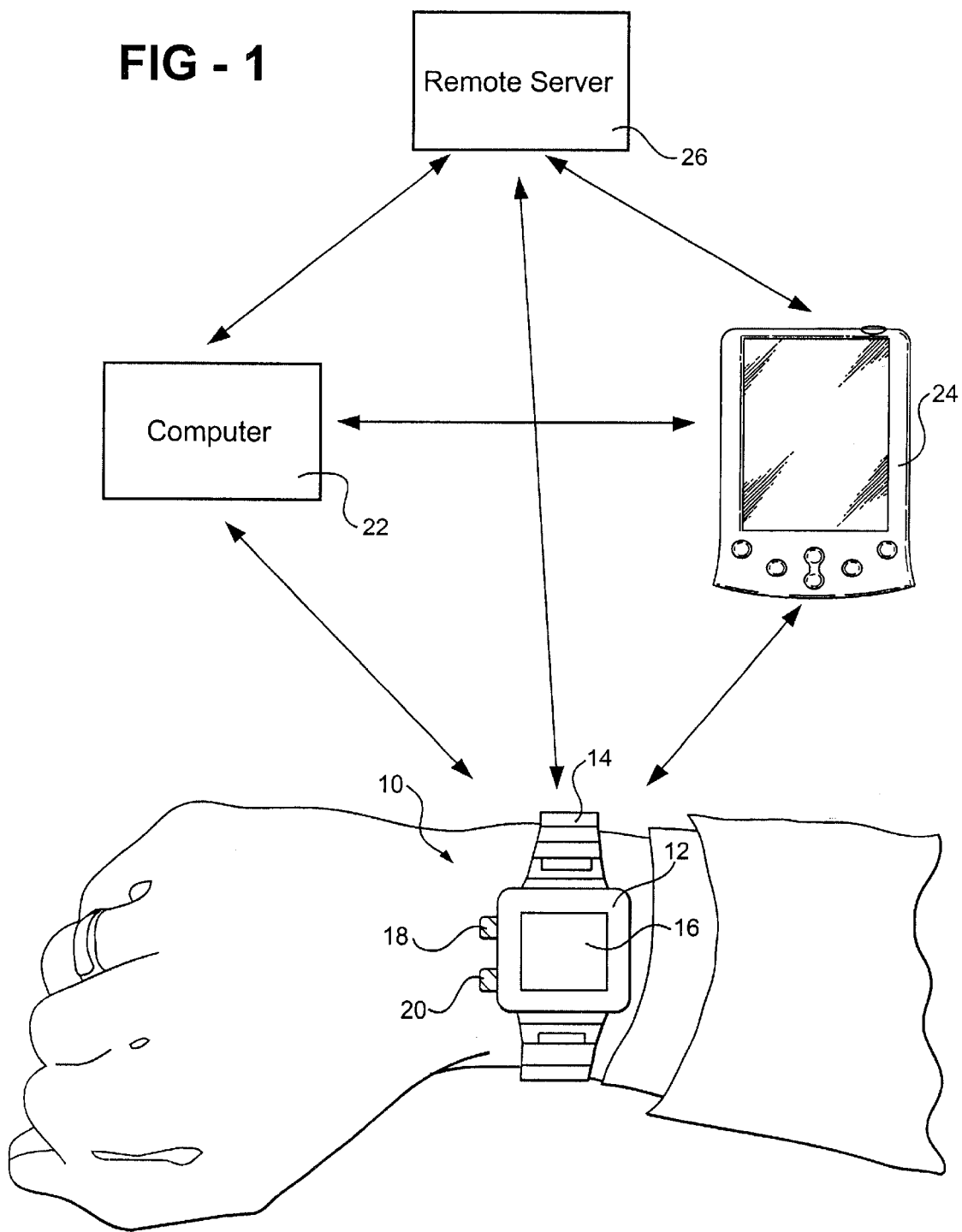
FIG. 1 is a view of a first embodiment of a diet and activity monitoring device and system schematically illustrating communication between the device and local and remote computers.

FIG. 1 illustrates a wrist-mounted embodiment of a diet and activity monitoring device 10 according to the present invention. Communication with remote and local computing devices is also shown schematically. The monitoring device 10 includes a case or housing 12 which connects to the wrist of a subject using a wristband 14. A display 16 is arranged on the front of the case 12 so that it can be periodically viewed by the subject. At least one control, such as button 18, is provided for controlling functions of the monitoring device 10. Additional controls, such as button 20, may also be provided. The monitoring device 12 is designed to be worn or carried by the subject during their daily activity to allow convenient and continuous monitoring of their daily activities and dietary consumption. The monitoring device 10 preferably includes the capability to communicate with local and remote computers using any of a variety of wired and wireless approaches. For example, the monitoring device 10 may communicate with local computer 22 by interconnecting a wire between the computer 22 and the device 10, or by "docking" the monitoring device 10 into a communications dock associated with computer 22. The monitoring device 10 may communicate with a personal digital assistant (PDA) 24 by docking therewith, or by wireless communication, such as infrared communication or with a wired connection.

For purposes of this disclosure, local computer 22 and PDA 24 are defined to include all computing devices, whether portable or stationary. This definition includes, but is not limited to, electronic books, laptop and handheld computers, cellular phones, pagers, desktop computers, and wearable computers. Communication may be provided between the monitoring device 10 and the PDA 24, with the PDA 24 later communicating with the local computer 22, or vice versa. The monitoring device 10 may also interconnect with remote server 26. For example, the monitoring device 10 may communicate with a web page running on a remote server via the Internet. The monitoring device 10 may include cellular or other wireless or wired communication capability so as to interconnect with the Internet either continuously or periodically. Communication with a remote server 26 may be via the local computer 22 or PDA 24. The monitoring device 10 may also include some type of memory chip or memory module that may be removed from the monitoring device 10 and inserted into the local computer 22 or the PDA 24 for transfer of data.

The compact size and wearability of the monitoring device 10 allows the subject to conveniently carry the device with them at all times. The device includes a body activity monitor, which may be integral with or separate from the housing 12. The body activity monitor monitors some aspect of the subject's body activity allowing the person's total activity or caloric expenditure to be reasonably determined. The body activity monitor may take several forms. For example, in one preferred embodiment, the body activity monitor includes a global positioning system (GPS) antenna and associated circuitry allowing the monitor to determine the position of the subject. By monitoring the changes in the subject's position throughout the day, a reasonable approximation of body activity may be made. Alternatively, the body activity monitor may take the form of a heart rate monitor. By monitoring the subject's heart rate over a period of time, a reasonable approximation of the subject's activity level may be determined. In yet another embodiment, the body activity monitor includes a motion sensor such as a one, two, or three axis accelerometer. By processing signals from the accelerometer, the body activity monitor can determine the motion of the monitoring device 10, and hence the subject, over a period of time. From this, a reasonable approximation of body activity may be obtained.

The device 10 also includes a consumption notation control that the subject operates to indicate when they consume food. For example, one of the buttons, 18 or 20, may serve as the consumption notation control. The subject presses the button each time they consume food. Alternatively, the subject may press the button once when beginning food consumption and again when done consuming food. Obviously, this process is significantly simpler than filling out of a food log at the time of food consumption. The device 10 stores the times of each consumption event as a food flag. The duration of these consumption events may also be stored. The resulting food flags may later be used to reconstruct and record the amount and types of food actually consumed. A mode control may also be provided, such as another button. The mode control may allow the subject to indicate whether the food is consumed is breakfast, lunch, a snack, etc. The consumption notation control may take other forms, such as an audio or video recording device and/or a bar code scanner. The subject may later use a local or remote computer or PDA to perform analysis of the data obtained by the monitoring device 10, and to reconstruct and recorded data such as actual foods consumed, caloric balance, calories burned and other factors.

Figure 2:
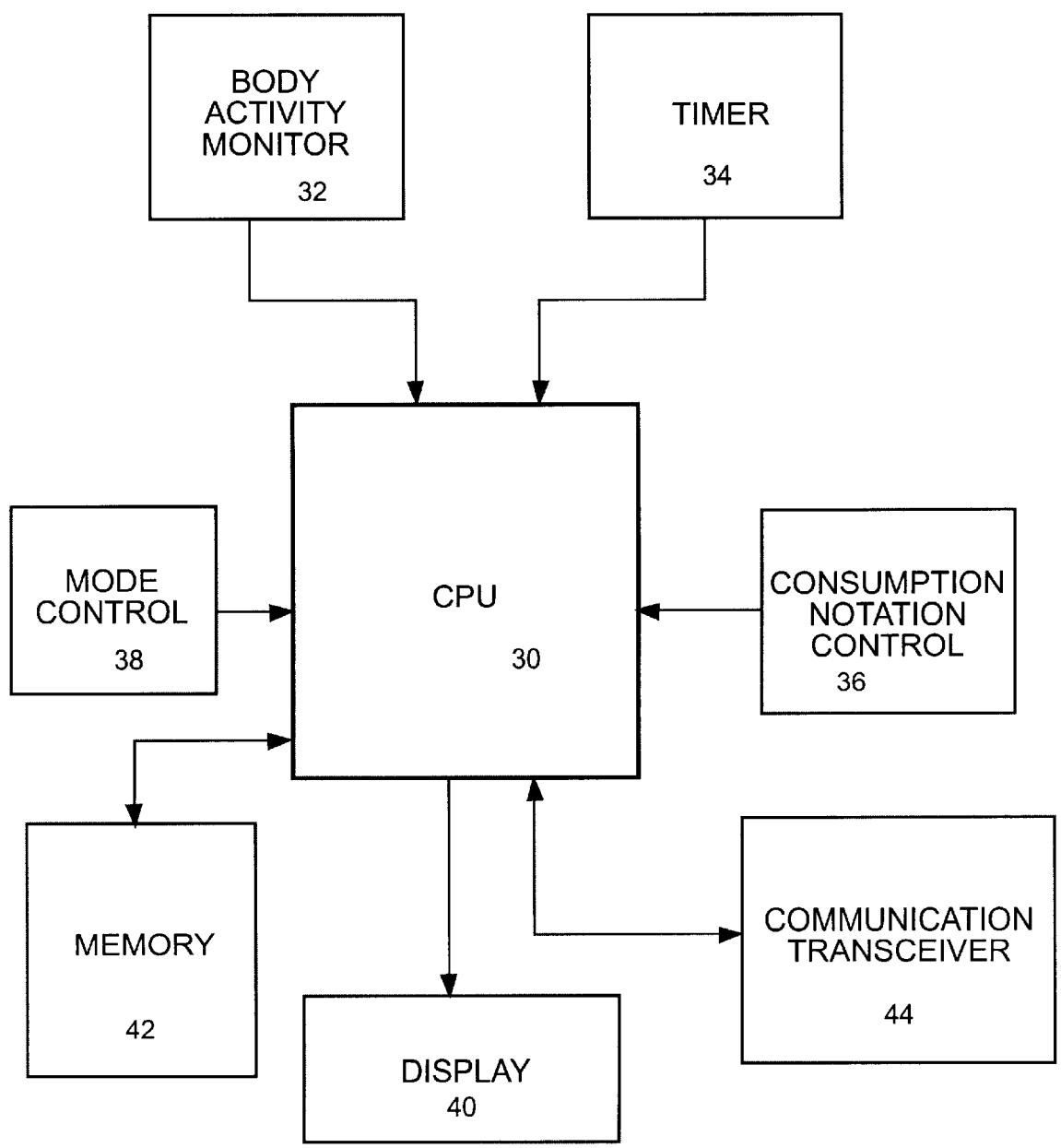
FIG. 2 is a schematic for a diet and activity monitoring device according to the present invention.

Referring now to FIG. 2, a monitoring device according to the present invention is illustrated schematically. As will be clear to those of skill in the art, the various components of a monitoring device according to the present invention may be housed within a single housing, or may include multiple discrete components. For example, body activity monitors may be separate from the remainder of the device. Also, some components of the monitoring device may reside in a local or remote computing device, with the wearable or carryable monitoring device serving as a recording device with very little or no processing power. However, the device preferably includes some type of processor such as a CPU 30 for processing and controlling the various signals. A body activity monitor 32 provides a signal indicative of the body activity of the subject to the CPU. A timer 34 outputs a time indicative signal to the CPU 30. A consumption notation control 36 provides an input to the CPU, allowing the subject to indicate when consumption occurs. An optional mode control 38, in communication with the CPU 30, may be used to switch between the various functions or displays of the device. The CPU 30 receives the signal from the body activity monitor and operates as an activity calculator to determine the body activity level for the subject. The CPU also serves as a consumption calculator by communicating with the consumption notation control and the timer to determine and store the times of the notation control as operated. The CPU 30 provides the data to display 40 for viewing by the subject. The memory 42 is interconnected with the CPU 30 and allows storage of data. Some form of communication is provided for the device, such as communication transceiver 44. This may be a wired or wireless transceiver.

Figure 3A:
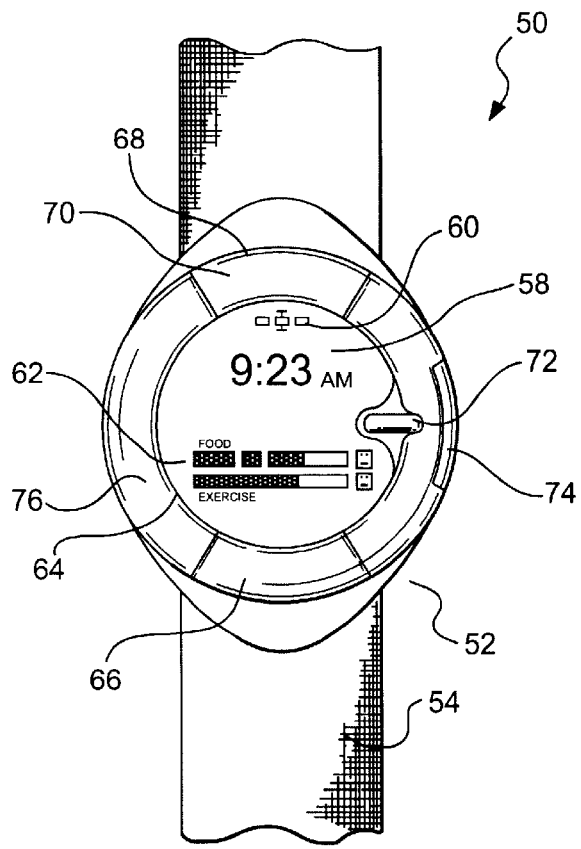
FIG. 3A is a front elevational view of a second embodiment of a diet and activity monitoring device according to the present invention.
Figure 3B:
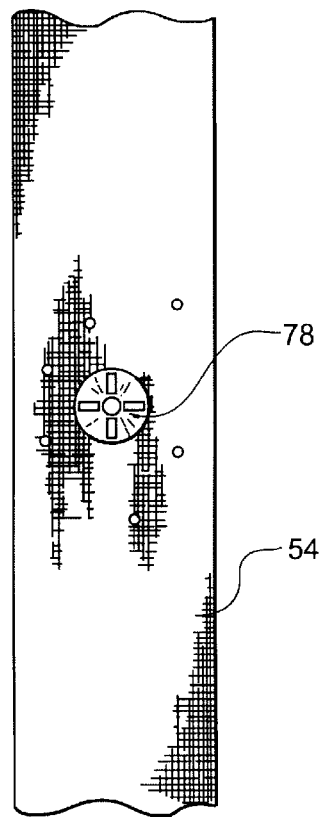
FIG. 3B is a rear elevational view of the strap portion of the diet and activity monitoring device of FIG. 3A.

Referring now to FIGS. 3A and 3B, a second embodiment of a wrist-mountable diet and activity monitoring device according to the present invention is generally shown at 50. The device 50 includes a case 52 with a strap 54 for interconnecting the device with the wrist of the subject. A display screen 56 includes a time display 58, a mode display 60, a food flag display 62 and an activity display 64. The perimeter of the case 52 provides a variety of buttons or controls, such as food flag button 66 that is operated to indicate when a consumption event has begun, and may also be used to indicate the termination of consumption. Microphone 68 may also be provided for recording sounds. In this embodiment, an infrared port 70 is provided next to the microphone 68. A mode button 72 is provided on the front face of the case 52 for switching the device between various operating modes. For example, the mode button may be used to determine whether a food flag or an activity flag is to be recorded and what type of food or activity is recorded. The sides of the case 74 and 76 may also form buttons for operating other functions such as initiation of infrared downloads and uploads. In some embodiments, the backside of the case 52 includes a heart rate sensor 78, as shown in FIG. 3B. As will be clear to those of skill in the art, there are a variety of approaches to determine heart rate using a wrist-mounted device. One preferred approach is photoplethysmography where an infrared light source and corresponding sensor measure infrared light either reflected from or transmitted through the wrists or other body part of the user. Other approaches such as pneumatic plethysmography, impedance cardiography, phonocardiography or electrocardiography may be used.

GPS Version of Monitor

As mentioned previously, the body activity monitor and the consumption notation control may each take a variety of forms. Therefore, multiple versions of a diet and activity monitoring device according to the present invention are possible. In one preferred embodiment, as shown in FIG. 4, the body activity monitor 80 includes a GPS antenna 82 and processing system for determining the position of a subject wearing or carrying the monitoring device 84 using GPS signals. In this embodiment, the device uses the GPS signals to periodically or continuously determine the location of the subject. A timer 86 is also provided for producing the time-indicative signal. A CPU 88 functions as an activity calculator 90, and receives a position indicative signal from the GPS-based activity monitor and time signal from the timer 86. Using these two signals, the activity calculator can determine changes in position of the subject as well as the rate of change in position. This allows a determination of movement or body activity. The position and time data and/or the body activity data are stored to memory 92. This in turn may be correlated with caloric expenditure and storage of correlated time and position data in memory, for use in determining whether the subject is gaining or losing weight. The device may be calibrated to determine caloric expenditure using a calorimeter, as described in co-pending patent application Ser. No. 09/684,440, incorporated herein by reference. Some or all of the CPU functionality may be in the monitoring device 84, a local or remote computer, or shared between them.

The device also includes a consumption notation control 94, such as a button or other control that the subject operates each time they consume food. The CPU 88 in the device also functions as a consumption calculator 96. The consumption calculator 96 receives a signal from the consumption notation control 94 and the time signal from the timer 86 and stores the time for each consumption occurrence in memory 86. Optionally, the device may require or allow the user to again operate the control 94 to signal that the consumption event has ended. In use, the subject interconnects the monitoring device 84 with a wrist or otherwise carries the device when they begin their daily activities. As the subject carries the device during their daily activities, it records where they have been and the times they have been there. Each time the subject consumes food, such as breakfast, a snack, or even a drink, they operate the consumption notation control, such as by pressing a button, to create a food flag. This data is stored in memory 92. Periodically, such as each evening or the end of each week, the subject transfers data from the monitoring device 84 to a local or remote computing device using communication transceiver 98. For example, the communication transceiver may be an infrared communication port that allows data to be transmitted to a local computing device that also includes an infrared port. Software on the computing device allows analysis and processing of the data from the monitoring device.

Figure 7:
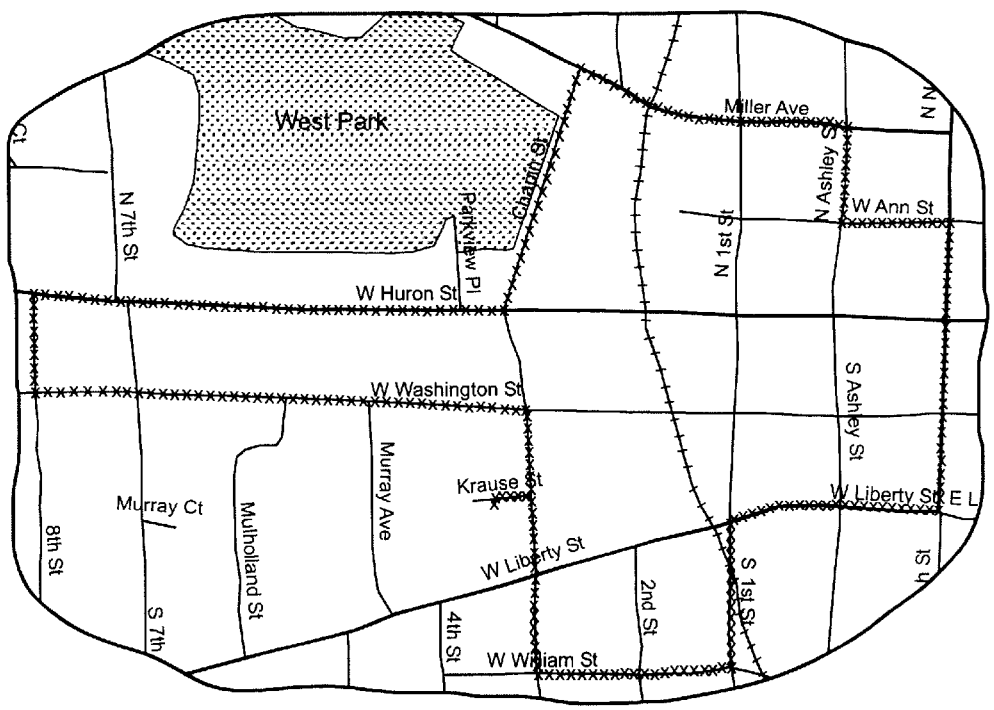
FIG. 7 is a view of a street level map illustrating a running route as tracked by the activity monitoring portion of one embodiment of the present invention.

FIG. 5 shows a sample screen display from a local computing device such as a home computer. In the upper left corner of the screen, a graph of activity level vs. time 100 is shown. This represents body activity data as determined by processing the position data from the GPS along with the time data from the timer. In the lower left corner of the screen is a location log 102 indicating the general position of the subject during the day. By comparing the activity level vs. time chart 100 with the location log 102, it can be seen that from 6:30 am to 7:14 am the subject went running, as indicated by a very high activity level. The location log indicates that the subject's location was "running route A: 4.3 miles at 5.7 mph." Because the GPS locates the subject continuously and periodically over time, the actual location of the subject with respect to known landmarks may be determined. In this example, it is assumed that this subject has previously run the same route. The first time the subject ran the route, the software on the computing device may have indicated that a high level of activity was performed but did not label the activity. The software may graph out the route followed by the subject, as shown in FIG. 7. The subject could then label this route as "running route A". Later, the subject may label other routes with other names. In analyzing the data received from the monitoring device, the software on the computing device determines that the route taken on this particular day corresponds to a route previously labeled as running route A. This subject's distance and running speed are also determined. As will be clear to those of skill in the art, other capabilities may be provided in the software. For example, the map of FIG. 6 may allow the user to zoom in and see actual speeds and times at various positions along the route. A caloric expenditure value may also be assigned to this amount of exercise at this rate, either based on estimates or based on a calibration using a calorimeter. For example, on one occasion, the subject may wear a portable calorimeter while running the route labeled "A" to record actual caloric expenditure during this running route. In the future, repetition of this running route is assumed to burn a similar number of calories. Speed changes may be compensated for by scaling the caloric expenditure up and down. As an additional alternative, calibration may be performed using a treadmill, either with or without a calorimeter. In one approach, the subject runs their route while wearing the monitoring device equipped with GPS or other locating capability. The route information, including distances, speeds, inclines, and declines are then transferred to a computer system that controls a treadmill. The subject may then run the same route on a treadmill programmed to duplicate the running route previously run. That is, the treadmill would duplicate the speeds, distances, inclines and declines of the actual running route. The treadmill or other computing system may then estimate calorie expenditure based on the speeds and inclines and declines. For example, some treadmills include the capability to estimate caloric expenditure based on a variety of factors. Alternatively, the subject may wear an indirect calorimeter while duplicating the running route on the treadmill. This simplifies the use of the calorimeter since the subject is not required to wear the calorimeter outdoors. Also, it allows the calibration process to be performed at a facility such as a gym.

Referring again to FIG. 5, it can be seen that the activity level returns to a low level up until about noon. During this time, the location log indicates the subject returned home for 45 minutes, commuted to their office, and spent the rest of the morning at the office. Once again, when the monitoring device according to the present invention, along with the software according to the present invention, is first used, the subject may provide names for various activities and locations. These locations are later recognized and labeled with more familiar names The activity level returns to a higher level from shortly before noon until about 1:00. During this time, the location log indicates "gym." At the gym, the subject may have performed any of a variety of exercises. For example, if the subject went for a walk on a track, the GPS tracks their location and the time and determines their activity level. However, a GPS based activity monitor may be poorly suited to some activities wherein the subject does not move their location, but does expend energy.

If the subject spends 45 minutes on a stationary bicycle, the subject may expend a significant amount of energy, but not move their location sufficiently to register on the GPS. Therefore, in some embodiments of the present invention, the monitoring device includes more than one activity-related monitor. For example, in the present embodiment including a GPS, the device may also include a heart rate sensor either as part of the device itself, as shown in FIG. 3B, or as an auxiliary unit such as a chest strap that wirelessly communicates with the monitoring device. The subject may wear the heart rate sensor at all times or may wear it only when performing activities for which the GPS will not provide an accurate indication of body activity. Referring again to FIG. 4, the activity calculator 90 then receives a signal from both the GPS based activity monitor 80 and the heart rate sensor 104, or may be set to receive only one of the signals. If the subject is using a piece of stationary exercise equipment, the heart rate signal will be elevated, but the GPS signal will indicate that the subject is stationary. In this case, the on-board processor, or the software in the local computing device determines that the subject is exercising on a stationary piece of equipment and determines an activity level and/or caloric expenditure based on the heart rate data. As another alternative, the monitoring device may include a mode control 106 allowing the subject to place it in a variety of different operating modes. Among these modes may be a selection of particular exercises and type of monitoring. For example, the subject may place the monitor in a "stationary bicycling mode" at the time the subject begins his activity. The timer 86 may also be used to time the duration of this type of activity. By combining the time and/or heart rate signal with the fact that the monitor is in a particular mode, the activity calculator 90 can determine an activity level and/or caloric expenditure. Once again, the device may be calibrated using a calorimeter. Alternatively, the device may create an "exercise flag" with a time stamp to serve as a reminder.

As another alternative, many pieces of exercise equipment include their own monitoring device. As shown in FIG. 4, the monitoring device 84 according to the present invention may communicate with the monitoring device 108 on the exercise equipment in order to obtain additional data. For example, a stationary bicycle may include an on-board computer that measures speed, duration, and other factors. This data may be transferred to the activity calculator 90 and used in determining activity level or caloric expenditure.

At some exercise facilities, the various exercise equipment is interconnected or networked to allow computerized recording of an entire workout. This data may also be transferred to the monitoring device. Alternatively, the monitoring device may include a mode wherein the subject can input an activity level or caloric expenditure. For example, if the gym includes a system that determines an activity level or caloric expenditure for a workout, the data output by this system may be manually input into the monitoring device 84 using manual input 110. The manual input 110 use various buttons or controls to set the input to the desired level. If the computer system at the gym indicates that the subject burned 1100 calories, the subject could toggle the display 112 on the monitoring device until it indicates that 1100 calories were burned. This data may be incorporated with the remaining activity level and used in calculating overall activity levels and caloric expenditures. The monitoring device may also save previous settings so that the next time the person is at the gym, they can just indicate that the same exercise was performed for the same amount of time, thereby minimizing the amount of manual input or data transfer. As yet another alternative, the data from the various exercise equipment or from the exercise facility may be directly transferred to the person's home computer or other computing device for incorporation into the overall monitoring system.

Referring again to FIG. 5, the activity level graph 100 shows a moderate level of activity while the subject is in the gym. This may be determined from GPS data or from other sensors. An additional type of sensor which may be provided for use with the present invention is an accelerometer or other type of motion sensor. This may be attached to the subject's belt to determine motion of the subject. This allows determination of activity levels on some "stationary" equipment. For example, if the subject is using a stair climbing exerciser, the subject's belt will experience movement that correlates with the subject's duration and intensity of exercise. A motion sensor 114 is shown in FIG. 4 communicating with activity calculator 90. Other sensors may be used as well. For example, a respiration sensor 105 may be used in place of or in addition to the other sensors to assist in determination of activity. Respiration rate and depth generally correlate with energy consumption. Therefore, monitoring a subject's respiration provides additional data useful in determining activity level. Respiration sensors may take several forms. For example, a chest strap may be used to measure expansion of the subject's chest. Alternatively, ultrasonic sensing may be used to measure expansion and contraction of a subject's chest. Aspects of ultrasonic-based sensors and monitoring are further described in co-pending patent application Ser. No. 09/669,125 and co-pending provisional patent applications Ser. Nos. 60/195,779, 60/206, 905, and 60/225,454, incorporated herein by reference. Respiration sensors are also available from Friendly Sensors of Germany. Respiration may also be sensed using a flow meter or an indirect calorimeter that the subject breathes through. Other types of respiration sensors may also be used.

Referring now to FIG. 6, an additional embodiment of a monitoring device according to the present invention is generally shown at 120. This embodiment differs from the previous embodiment in that it includes a position and/or activity discriminator 122 as part of or in communication with the body activity monitor 124. The discriminator 122 may take several forms, but functions to determine the position and/or activity of the subject using the monitor 120. To do so, the discriminator determines the proximity of the subject to various devices and locations, such as exercise equipment and buildings. In one embodiment, the discriminator 122 is a wireless transceiver, such as using the blue tooth protocol that recognizes and/or communicates with radio tags connected to various equipment. For example, a pair of running shoes, 126 may have a radio tag embedded in the shoes or connected thereto. Likewise, a radio tag may be part of or connected to a stationery bike 128, a road bike 130, or a pair of cross-country skis 132. When the discriminator 122 recognizes a proximity to the running shoes, this information is transmitted to the body activity monitor 124 and activity calculator 134. The monitor 120, or local or remote computing device used to process data from the monitor 120, then uses the information that the running shoes 126 were close to the monitor 120 during a certain period of time. In a simple version, this merely creates an exercise flag with a start and stop time corresponding to the duration of use of the running shoes. In more advanced embodiments, a signal may be received from a GPS 136, a heart rate sensor 138, and/or a motion sensor 140. Information from the discriminator 122 indicates the type of equipment being used and the body activity information from the GPS 136, the heart rate sensor 138, and/or the motion sensor 140 allows the activity calculator 134 to determine the type of activity being performed, the duration of the activity, and the intensity of the activity. Once again, the monitor 120 or the software on the local or remote computing device may be calibrated to improve the accuracy of the body activity level determined by the system. The discriminator 122 may also determine proximity to locations such as gym 142. For example, a gym may have a blue toothed-enabled transmitter allowing the discriminator 122 to determine proximity to the gym 142. Other locations may also be radio tagged. As one example, the discriminator 122 may determine that the subject is in the gym 142 and close to a stationery bike 128. Calibration data may be stored for this particular stationery bike 128. The various pieces of equipment may also transmit exercise data to the discriminator 122 to provide additional information for calculating activity level. For example, the running shoes 126 may include an embedded motion or force sensor which transmits to the discriminator 122 or body activity monitor 124 providing additional data on exercise parameters. As will be clear to those of skill in the art, other approaches to determining the proximity of the monitoring device 120 to various equipment and/or locations may also be used. The discriminator 122 may also be used to provide some of the functionality of a GPS, such as providing a location log 102 as shown in FIG. 5. This information may be used for activity as well as consumption, as will be discussed herein below. As will be clear to those of skill in the art, the discriminator may communicate with a wide variety of equipment. In addition, the discriminator may be programmed to recognize particular radio tags not previously programmed into the discriminator or the monitoring device. Additional sensors may also be provided and communicate with the body activity monitor either directly or through the discriminator. For example, motion sensors may be interconnected with the wrist and/or ankles of a subject with the sensors communicating with the monitoring device. This allows the monitoring device to record additional information as to body activity. Also, the sensors may be wired to the monitoring device, communicate wirelessly, or transfer data in a batch using a memory module or direct interconnection at a later time.

In FIG. 5, the activity level graph 100 shows that the activity level returns to a low level from 1:00 until shortly after 7:00. During this time, the subject, as indicated in the location log 102, returns to the office, commutes home, spends some time at home, and then goes out to eat. Obviously, the GPS will indicate that the subject has moved a significant distance when the subject is actually not exercising. For example, when commuting, the GPS unit will indicate significant movement by the subject, though this movement is not attributable to exercise. As discussed previously, when the subject first uses the system of the present invention, they may designate certain movement patterns as correlating with certain activities, such as commuting. Also, if the monitoring device according to the present invention includes more than one body activity monitor, such as heart rate sensor or motion sensor in addition to the GPS, the data from the additional sensors allows the system to determine whether motion is due to exercise or due to other factors, such as riding in an automobile. For example, when a person is driving, the GPS will show significant amounts of movement, but the heart rate sensor indicates that the subject is not exercising sufficiently to move this much.

It is preferred that the software used with the system according to the present invention learns over time to minimize the amount of input required of the subject. For example, the system has "learned" that travel over a particular route resulting in a particular set of data from the GPS or other sensors corresponds to commuting. Later, if the subject drives to a different location, the system determines that this is again a commuting activity, since the distance and speed are too great to correspond to running or bicycling. Also, the GPS system may provide data allowing the system to look up what actual locations are and determine the likely type of activity corresponding to movement in those areas. For example, if the GPS indicates that the person has moved from one city to another by a particular route, the system can determine whether the person traveled by automobile, train or airplane.

Figure 8:
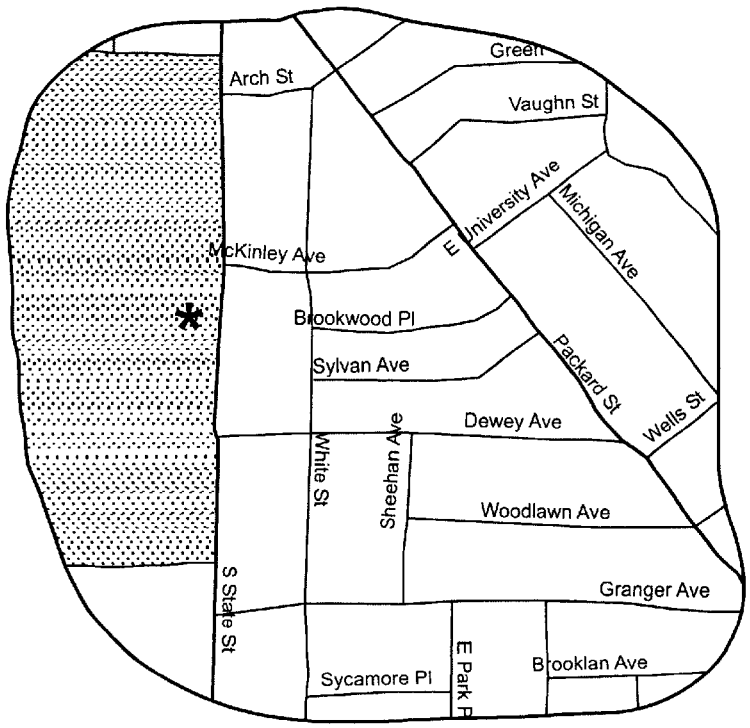
FIG. 8 is a view of a street level map illustrating a location indicator to assist a subject in locating where activity and/or consumption took place.

Returning to FIG. 5, there is again an increase in activity level beginning shortly after 7:00 extending to about 8:30. Looking at the location log, the location log indicates that the person was at an unknown location. This is the case where the subject has not previously been in the same location while using the system, or has not previously labeled the location. The system preferably provides the subject with an opportunity to view the location, as indicated. FIG. 8 shows a map with a location indicated where the subject was at the particular time. The system may look up this location in a database to determine what is located at the position, or the subject may input what they know about the location. In this example, we will assume that an ice skating rink is located at the location indicated on the map of FIG. 8. The subject may then return to the view of FIG. 5 and input that the unknown location is actually an ice skating rink. The activity level may then be correlated with a caloric expenditure or activity level based on the activity being ice-skating.

The monitoring device or the computing device may convert body activity, as sensed by any of the variety of activity monitors or sensors, to caloric expenditure, activity level of some type, points, or any other system. For example, points may be provided as part of a competition.

Referring again to FIG. 5, a food flag chart 150 is shown in the middle of the display and a consumption log 152 is shown in the lower right corner. Food flags are shown at the times during the day that the subject operated the consumption notation control 94. Five flags are shown. For each flag, the time and duration is shown in the consumption log. As mentioned previously, duration for each food flag is optional. The subject may indicate the time at which consumption begins and, optionally, when consumption ends. The display of FIG. 5 assumes that duration is known. Additionally, the food flags may be labeled as breakfast, snack, lunch, etc. based on the time of consumption. Alternatively, the mode control 106 on the monitoring device may be used to indicate what type of consumption, such as breakfast or snack, is occurring. Alternatively, more detailed modes may be provided so that the mode control may be used to indicate a more specific type of consumption, such as "salad and diet Coke". Preferably, the selection of modes are limited to those that the subject typically uses. An unlabeled or unknown label may also be used where a particular mode does not fit the consumption being undertaken. As shown in the consumption log 152, the first food flag occurs at 7:20 am and lasts for 20 minutes. A column is also given for location, as determined by the GPS if so equipped. This food flag occurred when the subject was at home. Based on previous entries, the software presents three choices for what was consumed during the first food flag. It indicates a breakfast A, breakfast B, and a custom entry. Breakfasts A and B are previous breakfasts eaten by the subject at home in the morning. Breakfast A is highlighted indicating that the software will default to choosing breakfast A if another choice is not made. The default choices may be based on previous behavior. For example, previous behavior shows that on most weekday mornings the subject eats breakfast A, while on weekend mornings, the subject eats breakfast B. A custom choice is also provided wherein the subject may enter an auxiliary screen where a variety of foods may be entered. Additional information on food logging, which may form part of the present invention, is disclosed in co-pending patent application Ser. No. 09/721, 382, filed Nov. 22, 2000, incorporated herein by reference.

Returning to the consumption log 152, the second food flag occurs at 12:50 and lasts for 10 minutes. The location is given as the gym. Based on previous behavior, the software suggests two possible lunches that the subject may purchase at the gym, as well as a custom option. Once again, one choice is highlighted as the default choice. The third food flag indicates a snack at about 4:00 pm at the office and a variety of choices are given based on past behavior.

At 6:25 pm a food flag occurs and lasts for 35 minutes. The location for this food flag is Tony's Pizzeria. As with the activity level and location log, the subject may have given labels to locations where meals were eaten. In this case, the subject has previously eaten at Tony's Pizzeria and has two typical meals labeled as dinner T1 and dinner T2. A custom choice is also provided that allows the subject to view the menu from Tony's Pizzeria. According to an additional aspect of the present invention, the software may include menus for a variety of restaurants including typical fast food restaurants and restaurants in the subject's home location. Also, electronic menus may be provided by individual restaurants that participate in a program run by the distributor of the present system. Menus may also be distributed via the Internet with the menus provided by the software provider, other providers, individuals, or the restaurant itself. When the subject first visited Tony's Pizzeria, the system identified the location based on the GPS signal. In this case, the electronic menu, if available, may be presented allowing the subject to pick the items they actually consumed. Alternatively, the location may have been unknown and the subject may have inputted the name, as well as the foods eaten. The final food flag is another snack, which was eaten at home. Suggestions are provided and one suggestion is highlighted as the default choice.

The monitoring device or the computing device can use the information from food consumption or food flags to determine caloric intake or energy intake in other units. For example, Weight Watcher® points may be used. The monitoring device may include a button dedicated to the input of Weight Watcher® points or may include a mode for entering Weight Watcher® points. Such an approach may also be used with the local computing device for recording of food consumption. Also, other point systems or measuring systems may be used.

As will be clear to those of skill in the art, the combination of the monitoring device and the software as just described provides a very simple approach for monitoring diet and activity. Even the subject who makes minimal use of the system, will still have significantly more information about diet and activity than without the system. Also, through minimum interaction with the system, the subject may make the system recognize particular activities and make it very simple to choose particular foods consumed each day. If the subject does not have enough time to review the suggested food choices on a particular day, the software, based on learning from past behavior, can make a reasonable estimate of food consumed, based on locations and times of the food flags.

In a simpler version of the present invention, the food flags may consist merely of time and/or duration flags without the software providing suggested meals. Even so, the food flags provide a valuable reminder as to what was eaten on a particular day. For example, if a subject knows that they consumed food five different times on a particular day, and what those times were, it is less likely they will forget to record a particular meal in a food log. Provision of location data, in some embodiments, provides even more of a reminder.

In another embodiment of the present invention, the diet and activity monitoring device is provided with an audio or video recording capability either in place of in addition to a button which is pressed for food flags. An audio/video input 95 is shown in FIG. 4. An audio signal may be digitally recorded onto a memory device in the diet and activity monitor. When the subject consumes food, they can push a record button and speak into a microphone on the monitoring device. The digital recording is stored for later playback to help the subject reconstruct what was eaten at a particular meal. For example, following a meal, the subject may record "large salad, low fat ranch dressing, iced tea." Later, the subject may play back this recording either from the monitoring device itself or from the local or remote computing device. The subject may then log the foods that were eaten. The time and location of the recording may also be noted by the device. Alternatively, the local or remote computing device may include voice recognition capability so as to change the voice recording into a typed message, or to interpret the message and to determine what was actually eaten. For example, following lunch, the subject may record lunch A and a system will later interpret this to mean that the subject consumed a meal previously designated as lunch A.

In one embodiment of the present invention, the monitoring device 84 includes wireless communication, such as a cellular communication, or as part of a cellular telephone. Audio recording capability is provided by a simplified interconnection to a remote device that records whatever is spoken into the monitoring device. For example, if the monitoring device is part of or an accessory to a cellular telephone, the cellular telephone can speed dial a telephone number connected to a recording device. The subject then speaks into the cellular telephone as if making a phone call and the remote location records what is spoken. The audio recording may be transmitted to a local or remote computing device where additional processing is provided. Video recordings may also be transmitted wirelessly for additional processing.

As known to those of skill in the art, digital still and motion cameras are becoming increasingly compact. Wrist watch-based digital cameras are known in the art. For example, an optical imaging sensor and an imaging control may be provided to capture pictures. This capability may be incorporated into the monitoring device according to the present invention, allowing the subject to take a picture of food to be consumed. This capability may be in addition to, or substitute for, a button or audio recording. Once again, time and/or location may be recorded. This picture may be later displayed as a reminder when logging foods, or the picture may be processed by the computer to help determine what foods were consumed, or an administrator of the system may view the picture and input foods consumed for the subject under some type of subscription program. These aspects of the present invention are further explored in co-pending provisional patent application Ser. No. 60/230,860. Bar code scanning or image recognition may also be provided to create food flags and to record information about consumption. The monitoring device may also communicate with other devices such as scanners at a grocery store to transfer information concerning foods purchased or consumed. Information may also be directly transmitted from a device at a place of consumption, such as a restaurant, concerning the food consumed by the subject. For example, the subject enters a restaurant and orders a meal. After ordering or consuming the meal, a computer at the restaurant transmits information concerning the consumption to the monitoring device. The monitoring device may also communicate with or interconnect with a food scale for recordation of food quantity as described in co-pending provisional patent application Ser. No. 60/234,866, incorporated herein by reference.

In some embodiments of the present invention, body activity monitoring may be dispensed with. Instead, the monitoring device serves as a diet monitoring device and includes any or all of the above capabilities, such as creation of food flags, audio recording and video recording. In embodiments of the present invention that do include body activity monitoring, audio or video recording may also be used to note exercise conducted. For example, the subject may record a note saying, "stationary bike, 400 activity points". This allows a simple approach to recording exercise data displayed by the stationary bicycle at the completion of exercise and may be later used to determine an activity level. Also, voice recording may be used to indicate the start and end of exercise. For example, if the subject goes swimming, they may record a brief note saying "begin swimming" when they start their exercise. Later, at the completion of the exercise, they may record a note saying "end swimming, 10 laps". Timestamps associated with audio recordings allow determination of the duration of exercise. Once again, voice recognition may be used to enhance the capabilities of the system. These same features may be used in the embodiments that include body activity monitoring as well.

As mentioned previously, body activity monitors other than a GPS-based tracking device may be provided in addition to or in place of the GPS. In one embodiment, the monitoring device according to the present invention includes a motion sensor and/or heart monitor that allows determination of activity and/or caloric consumption. By recording body motion and/or heart rate throughout the day, activity level may be determined. In addition, a motion sensor allows determination of additional data concerning exercise, such as intensity and type of activity. That is, if the motion sensor includes an accelerometer, the accelerometer will output a signal indicating the motion experienced by the accelerometer. The signal will have certain shapes depending on the activity undertaken. While riding in an automobile, the accelerometer will experience certain vibrations and movement indicative of transport by automobile. When climbing stairs, a different signal will be created. Running or walking will create yet other signals. At the end of the day, a chart may be created of the motion experienced by the accelerometer throughout the day. Software on a local or remote computer device can process the signal to determine activity levels. The user may also input activities conducted at various times and calibrate the signal using an indirect calorimeter. Similar considerations apply to the use of a heart rate monitor. Generally, heart rate correlates with body activity and expenditure of energy. At the end of the day, the heart rate signal may be downloaded and processed to determine activity level. Inclusion of more that one type of activity monitor such as a GPS and a heart rate monitor, allows increased accuracy in the collection of additional data. Also, activity data may be processed to help in the determination of consumption. For example, when a person consumes a meal, it is typical for them to sit still during the meal. Also, their location may indicate that consumption is occurring. For example, if the body activity data indicates that the subject has sat still for twenty minutes in a location known to be a fast-food restaurant, a food flag may be automatically created.

Figure 9:
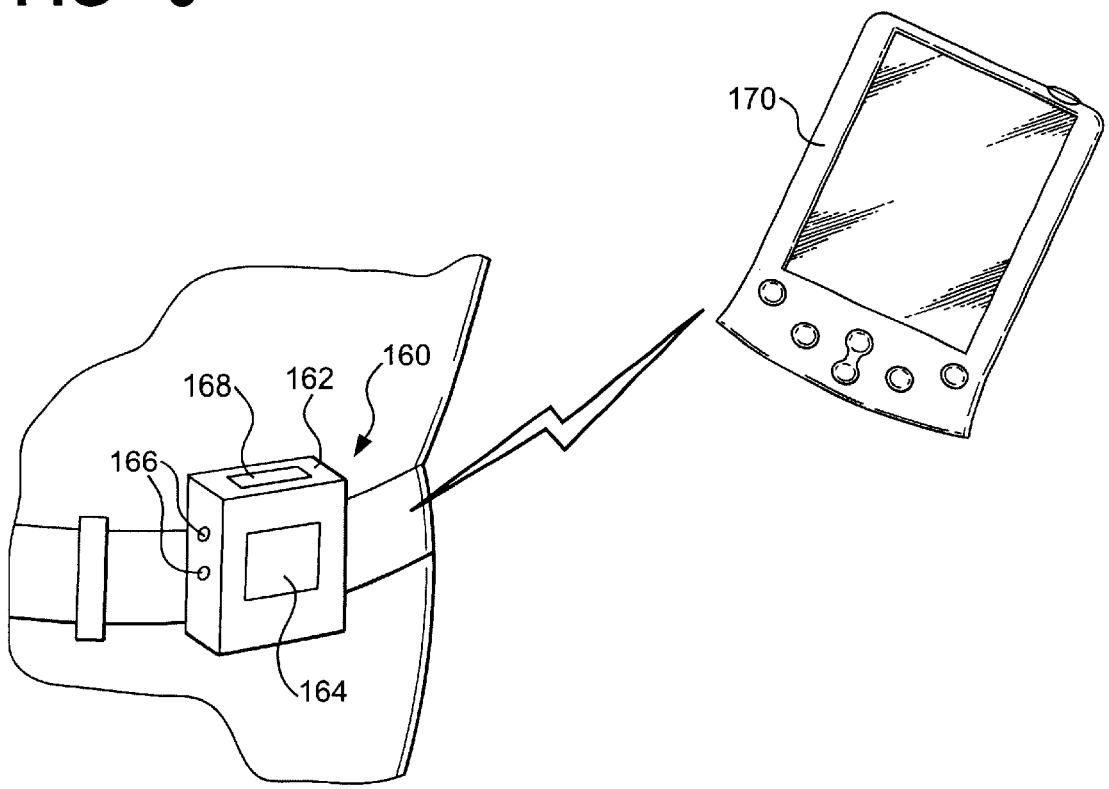
FIG. 9 is a perspective view of an additional embodiment of a diet activity monitoring device according to the present invention mounted on the belt of a subject and illustrating wireless communication with a personal digital assistant.

Referring now to FIG. 9, a belt-mounted embodiment of a monitoring device according to the present invention is generally shown at 160. The device includes the housing 162 with the display 164 and one or more controls 166. A memory module 168 may be provided for storage and transfer of data. A PDA 170 is also illustrated in wireless communication with the monitoring device 160. A belt-mounted version of the present invention is particularly well suited to the use of an accelerometer or other motion sensor as a body activity monitor because movement of a subject's belt closely correlates with their body activity. The device may also be detachable from the belt to connect with other devices or to allow voice or video recording. The controls 96 may be manipulated to create food flags or exercise flags or to change the operating mode of the device. FIG. 8 illustrates an additional, more stylized version of a belt-mounted or clothing-mounted monitoring device according to the present invention.

The monitoring device according to the present invention may take other forms. For example, the monitoring device may be a PDA that includes or communicates with a body activity monitor. The PDA may have an accelerometer built in or interconnected therewith, as described in co-pending patent application Ser. No. 09/669,125, incorporated herein by reference. Use of the PDA as the monitoring device allows enhanced functionality at the cost of additional bulk. For example, in addition to recording food flags, the PDA could be used to log actual foods consumed either at the time of consumption or later. Also, additional information may be easily input as to activity level.

As mentioned previously, it is preferred that a subject obtain their resting energy expenditure using an indirect calorimeter. Information concerning resting energy expenditure may be transferred to the computing device or uploaded to the monitoring for display to the user. A resting energy expenditure may also be obtained from other less preferred sources. There are several approaches to determining the resting expenditure and/or total energy expenditure, each with varying degrees of accuracy. A traditional approach to calculating resting energy expenditure is the use of equations or charts. A computer model may also be created for a person based on their height, weight, sex, age etc. and a prediction may be made for resting energy expenditure. Activity energy expenditure may also be scaled up and down based on resting energy expenditure. That is, it may be assumed that a smaller person with a lower resting energy expenditure will expend less energy when involved in an activity such as walking than a larger person with a larger resting energy expenditure. Because the system according to the present invention collects a large amount of data, resting energy expenditure and activity energy expenditure may be adjusted based on this data. For example, a system according to the present invention includes additional information about the person such as age, sex, weight, etc. Also, it is preferred that the tracking data is input periodically, such as body weight and/or body fat percentage. This data may be obtained by a bathroom scale or other devices and manually input to the system or wirelessly communicated. By tracking recorded food intake, recorded activity level, and resting energy expenditure, a prediction of body weight and body fat changes may be made. By tracking actual changes in body weight and body fat, adjustments may be made in the predicted algorithms or the assigned values for resting energy expenditure, activity energy expenditure or the consumption may be adjusted. For example, the system can learn that a particular user, while measuring a high resting energy expenditure using an indirect calorimeter, actually has a lower resting energy expenditure as evidenced by the slower loss of weight. This may be due to improper use of the indirect calorimeter or other factors. Alternatively, the system may adjust the calorie expenditure assigned to various activities undertaken by the user. Such adjustments can result in much more accurate prediction on weight loss and success with a weight management program.

Figure 10:
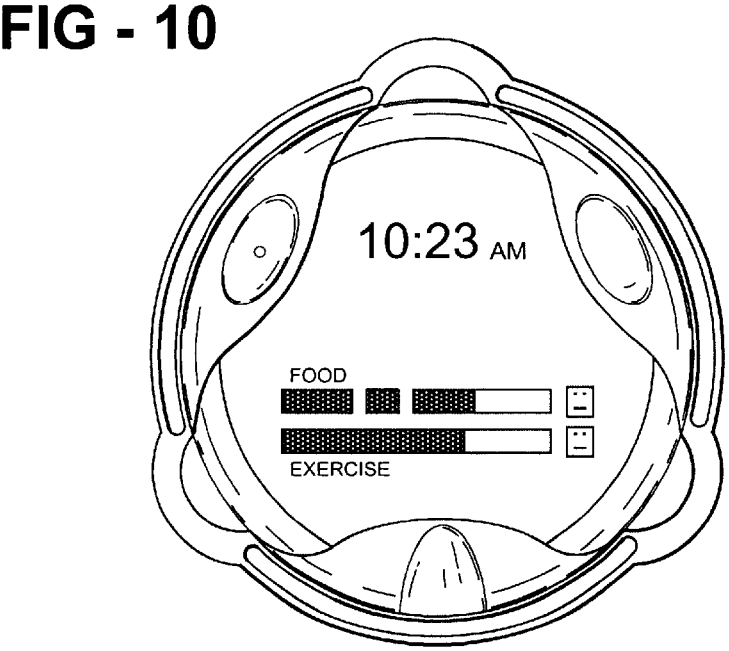
FIG. 10 is a front elevational view of an additional embodiment of a monitoring device according to the present invention.

Once resting energy expenditure is known, the monitoring device may then display calorie balance, which is the difference between calorie consumption and total energy expenditure. Total energy expenditure is determined by adding the activity energy expenditure to resting energy expenditure. Caloric consumption is determined from food consumption. The monitoring device may make various assumptions concerning consumption and/or activity energy expenditure in order to provide a real time or periodic caloric balance. For example, the monitoring device may assume a certain number of calories consumed each time a food flag is created, or food flags may be provided with various values based on the time of consumption or other data. If activity level is monitored throughout the day, an estimate of caloric expenditure may also be determined for use in determining a caloric balance. A variety of approaches may be used to show progress of the user. For example, in FIG. 10, the monitoring device has a display showing a bar graph for food and a bar graph for exercise. These bar graphs may be used to show progress towards a goal or caloric balance. For example, in order to meet an activity expenditure target, the subject needs to exercise until the bar graph moves to its full length. A food bar graph may be sized such that the subject attempts to limit their consumption such that the bar graph does not extend completely to the right side. Also, the monitoring device may display information from previous days showing caloric balance for individual days or weeks, etc. This information may be uploaded from the local or remote computing devices back to the monitoring device for display to the user. The present invention may also be used as part of a feedback system as described in co-pending patent application Ser. No. 09/685,625, incorporated herein by reference.

As will be clear to those of skill in the art, the present invention may be altered in various ways without departing from the scope or intent of the present invention. It is the following claims, including all equivalents, which define the scope of the present invention.

We claim:

1. A device for monitoring the diet and activity of a subject comprising:
    a timer operable to output a time indicative signal;
    a body activity monitor for monitoring the body activity of the subject, the body activity monitor operable to output a signal indicative of the body activity of the subject;
    a consumption notation control operable by the subject to indicate when the subject consumes food;
    an activity calculator operable to receive the body activity indicative signal and to determine a body activity level for the subject; and
    a consumption calculator in communication with the consumption notation control and operable to receive the time indicative signal, the consumption calculator further operable to determine and store the times when the consumption notation control is operated; and
    the body activity monitor comprising a heart rate monitor operable to determine the heart rate of the subject, the body activity indicative signal being a heart rate indicative signal.

2. The monitoring device according to claim 1, wherein the body activity monitor further comprises:
    a motion sensor operable to determine the motion of the subject, the body activity indicative signal being a body motion indicative signal.

3. The monitoring device according to claim 1, wherein the body activity monitor further comprises:
    a GPS based tracking device operable to determine the position of the subject, the body activity indicative signal being a position indicative signal; and
    the activity calculator further being operable to receive the time indicative signal, the activity calculator determining the body activity of the subject by determining the changes in the position of the subject over a period of time.

4. The monitoring device according to claim 1, wherein the body activity monitor further comprises:
    a respiration sensor operable to sense respiration of the subject.

5. The monitoring device according to claim 1, wherein the consumption notation control comprises:
    an audio recorder operable to receive audio notations from the subject.

6. The monitoring device according to claim 1, wherein the consumption notation control comprises:
    a digital camera.

7. A portable device for recording diet and activity data for a subject, the device comprising:
    a housing configured to be carried by the subject;
    a display for displaying information to the subject;
    a body activity monitor operable to monitor the body activity of the subject;
    an input operable by the subject to note when food consumption occurs;
    a timer operable to output a time indicative signal;
    a processor in communication with the input and operable to receive the time indicative signal, the processor further operable to determine and store the times when the input is operated by the subject;
    a microphone; and
    a microphone control, the microphone control operable to receive and store an audio signal from the microphone whereby the subject can record an audio notation.

8. The device according to claim 7, further comprising voice recognition software operable to convert the audio signal into data representative of a text message.

9. The device according to claim 7, further comprising an optical imaging sensor and an imaging control, the imaging control operable to receive and store an optical signal from the imaging sensor.

10. The device according to claim 7, wherein the body activity monitor comprising a locating device operable to determine the location of the subject carrying the device.

11. The device according to claim 10, wherein the locating device is a global positioning system based locating device.

12. The device according to claim 10, wherein the body activity monitor is further operable to receive the time indicative signal and to determine the rate of change in the location of the subject and the body activity of the subject.

13. The device according to claim 7, wherein the body activity monitor comprises a heart rate monitor.

14. The device according to claim 7, wherein the body activity monitor comprises a body motion sensor.

15. The device according to claim 7, wherein the body activity monitor comprises a respiration sensor operable to sense respiration of the subject.

16. The device according to claim 7, further comprising a communication transceiver for communicating with a computing device.

17. A system for creating a consumption log for a subject comprising:
a portable device having a timer operable to output a time indicative signal and a consumption notation control operable by the subject to indicate when the subject consumes food, the portable device further having a processor in communication with the consumption notation control and operable to receive the time indicative signal, the processor further operable to determine and store the times when the consumption notation control is operated, the portable device further having a communication transceiver for transferring data indicative of the times when the consumption notation control was operated; and
a computing device having a display and a communication transceiver for receiving data from the portable device, the computing device operable to receive the data from the portable device, to display the times the consumption notation control is operated, and to display consumption choices for each time the consumption notation control is operated.

18. The system according to claim 17, wherein the computing device is further operable to create a consumption log and to determine caloric consumption for the subject.

19. The system according to claim 17, wherein the portable device further comprises a body activity monitor operable to monitor the body activity of the subject and to store data indicative of the body activity of the subject, the communication transceiver further operable to transfer the data indicative of the body activity.

20. The system according to claim 19, wherein the computing device is further operable to display information corresponding to the data indicative of the body activity.

21. The system according to claim 20, wherein the computing device is further operable to create an activity log and to determine an activity level for the subject.

22. A method of creating a consumption log for a subject comprising:
providing a portable device having a consumption notation control operable by the subject to record the times that the subject consumes food;
operating the consumption notation control each time the subject consumes food to record the consumption time;
providing a computing device operable to display consumption choices for each time the consumption notation control is operated, and to receive the recorded consumption times from the portable device;
transferring the recorded times to the computing device;
displaying the recorded times to the subject; and
recording foods consumed for each of the recorded times.

23. The method according to claim 22 further comprising the step of learning a consumption choice prior to said step of providing a computing device.

24. The method according to claim 22 further comprising the steps of:
monitoring an activity level of the subject using a body activity monitor and transmitting a signal to said computing device representative of the monitored activity level of the subject;
deetermining an activity level of the subject using the monitored activity level; and
using the monitored activity level and food consumption for the recorded times to determine a calorie balance for the subject.

25. The method according to claim 24 further comprising the step of learning an exercise prior to said step of monitoring an activity level.

26. A device for monitoring the diet and activity of a subject comprising:
a processor having a memory and a communications transceiver;
a timer operable to transmit a time indicative signal to said processor;
a body activity monitor for monitoring the body activity of the subject, the body activity monitor operable to transmit a signal to said processor indicative of the body activity of the subject;
a consumption notation control operable by the subject to indicate the subject is consuming food and is operable to transmit a food consumption signal to said processor;
an acitivity calculator within said processor that calculates a body activity level for the subject using the body activity signal; and
a consumption calculator within said processor that receives the consumption notation control signal and the time indicative signal, and uses the consumption notation control signal and time indicative signal to determine and store in the memory a duration of time the subject consumes food or engages in an activity, wherein the communications transceiver transmits the duration of time the subject consumes food or engages in an activity to a remote computing device.

27. The monitoring device according to claim 26 wherein the body activity monitor is a heart rate monitor supported on the body of the subject and operable to determine the heart rate of the subject, and transmit a signal representative of the heart rate of the subject to said activity calculator within said processor.

28. The monitoring device according to claim 26, wherein the body activity monitor is a motion sensor operable to sense motion of the subject and transmit a signal representative of the sensed motion to said activity calculator within said processor.

29. The monitoring device according to claim 26, wherein the body activity monitor is a Global Positioning System based tracking device operable to determine the position of the subject and transmit a signal representative of the position of the subject to said activity calculator within said processor, wherein said activity calculator uses the changes in the position of the subject over a period of time to determine the body activity level of the subject.

30. The monitoring device according to claim 26, wherein the body activity monitor is a respiration sensor operable to sense respiration of the subject and transmit a signal representative of the sensed respiration to said activity calculator within said processor, wherein said activity calculator uses the sensed respiration of the subject over a period of time to determine the body activity level of the subject.

31. The monitoring device according to claim 26 wherein the consumption notation control is an ausio recorder operable to receive audio input from the subject and transmit a signal representative of the audio input to said processor.

32. The monitoring device according to claim 26, wherein the consumption notation control is a digital video recorder operable to receive video input from the subject and tranmit a signal representative of the video input to said processor.

33. The monitoring device according to claim 26 wherein said remote computing device is a personal digital assistant.

34. The monitoring device according to claim 26 wherein activation of said consumption notation control sets a flood flag in the memory of said processor as a reminder of the amount and type of food consumed at that time by the subject.

35. The monitoring device according to claim 26 further comprising a mode control in communication with said processor for setting an operating mode of the monitoring device.

36. The monitoring device according to claim 26 further comprising a display operatively in communication with said processor for displaying monitored information to the subject.

37. The monitoring device according to claim 26 wherein activation of said body activity monitor sets an activity flag in the memory of said processor as a reminder of the amount and type of activity the subject participated in at that time.

38. The monitoring device according to claim 26 wherein said activity calculator is operatively in communication with a remotely located discriminator which tranmits an input signal representative of a known activity for use by the activity calculator in determining the activity level of the subject.

39. The monitoring device according to claim 26 wherein said remote computing device calculates a calorie balance for the subject from the subject's calorie intake and activity level, and the calorie balance is displayed on the display screen.

* * * * *

UNITED STATES PATENT AND TRADEMARK OFFICE
CERTIFICATE OF CORRECTION

PATENT NO. : 6,513,532 B2
DATED : February 4, 2003
INVENTOR(S) : Mault et al.

It is certified that error appears in the above-identified patent and that said Letters Patent is hereby corrected as shown below:

Column 1,
Lines 15-20, delete "This application also claims priority from U.S. patent application Ser. Nos. 09/685,625, filed Oct. 10, 2000; 09/630,398 filed Aug. 2, 2000; 09/669,125 filed Sep. 25, 2000; 09/684,440 filed Oct. 10, 2000; and 09/721,382 filed Nov. 22, 2000, are also incorporated herein in their entirety by reference".

Column 16,
Line 43, after "60/230,860" insert -- incorporated herein by reference. --.

Column 21,
Line 66, replace "deetermining" with -- determining --.

Column 22,
Line 62, replace "ausio" with -- audio --.

Column 23,
Line 1, replace "tranmit" with -- transmit --.

Signed and Sealed this

Second Day of September, 2003

JAMES E. ROGAN
*Director of the United States Patent and Trademark Office*